United States Patent [19]

Moore et al.

[11] Patent Number: 5,437,612
[45] Date of Patent: Aug. 1, 1995

[54] ANTIDECUBITUS IMMOBILIZATION CERVICAL COLLAR

[75] Inventors: George E. Moore, Jerrersontown, Ky.; Lisa A. G. Tweardy, Mt. Laurel, N.J.

[73] Assignee: The Jerome Group, Mt. Laurel, N.J.

[21] Appl. No.: 909,963

[22] Filed: Jul. 7, 1992

Related U.S. Application Data

[63] Continuation of Ser. No. 619,040, Nov. 28, 1990, Pat. No. 5,180,361.

[51] Int. Cl.⁶ .............................................. A61F 5/055
[52] U.S. Cl. ..................... 602/18; 128/DIG. 23
[58] Field of Search ................. 128/DIG. 23; 602/18, 602/21

[56] References Cited

U.S. PATENT DOCUMENTS

| | | | |
|---|---|---|---|
| 2,911,970 | 10/1959 | Bartels | 128/75 |
| 3,042,027 | 7/1962 | Monfardini | 602/18 |
| 3,135,256 | 6/1964 | Gruber | 128/75 |
| 3,220,406 | 11/1965 | Connelly | 128/75 |
| 3,285,244 | 11/1966 | Cottrell | 128/75 |
| 3,512,523 | 5/1970 | Barnett | 128/75 |
| 3,572,328 | 3/1971 | Bond | 128/75 |
| 3,916,885 | 11/1975 | Gaylord | 128/75 |
| 3,921,626 | 11/1975 | Neel | 128/75 |
| 4,099,523 | 7/1978 | Lowrey | 128/75 |
| 4,413,619 | 11/1983 | Garth | 602/18 |
| 4,520,801 | 6/1985 | Lerman | 128/75 |
| 4,538,597 | 9/1985 | Lerman | 602/18 |
| 4,940,043 | 7/1990 | Burns et al. | 128/75 |
| 4,961,418 | 10/1990 | McLaurin-Smith | 602/21 |
| 5,038,759 | 8/1991 | Morgenstern | 128/75 |

OTHER PUBLICATIONS

E-Collar; Believed before Nov. 28, 1990.
Zimmer EMS; Believed Before Nov. 28, 1990.
Exo-Static with Contact Closure and Chin Piece; Believed Before Nov. 28, 1990.
Exo-Static Collar; Believed Before Nov. 28, 1990.
Myo-Cervical Collar; Believed Before Nov. 28, 1990.
Cervical Collar with Adjustable Chin Piece; Believed Before Nov. 28, 1990.
Rigid Cervical Collars; Believed Before Nov. 28, 1990.
Adjustable Ortho-Collar; Believed Before Nov. 28, 1990.
Philadelphia Cervical Collar; dated May 1988.
Statneck; dated 1988.

*Primary Examiner*—Lynne A. Reichard
*Attorney, Agent, or Firm*—Ratner & Prestia

[57] ABSTRACT

A cervical collar is provided which has front and rear semi-rigid portions, attached by hook and loop fasteners. The front portion comprises a semi-rigid preformed jaw support contoured to follow the jaw line of a patient, and a preformed sternum brace contoured to contact the sternum and upper trapezius of the patient and to support said jaw support. The rear portion of the cervical collar is contoured to follow the curve of the back of the head or occiput and to support the head and neck. The sternum brace has right, left, and central sections, wherein the height of the central section is adapted to correspond to the distance between a patient's sternum and jaw at the chin and the height of the right and left sections is adapted to correspond to the distance between a patient's upper trapezius muscle and jaw. The height of the right and left sections is independent of the height of the central section. Further, the jaw support may include a cushioning pad and a covering of anti-decubitus material. In a preferred embodiment, the jaw support of the collar is adjustable, to adjust to the natural angle of the patient's jaw.

7 Claims, 10 Drawing Sheets

ANTIDECUBITUS IMMOBILIZATION CERVICAL COLLAR

This application is a continuation of application Ser. No. 07/619,040, filed Nov. 28, 1990, now U.S. Pat. No. 5,180.361.

BACKGROUND OF THE INVENTION

Various types of cervical collars have been developed for treating conditions of the neck and cervical spine. Some of these collars are intended merely as support for whiplash and other such injuries where support for the head and neck is needed. The primary objective for the use of such a collar is to partially immobilize the head and neck, to provide support for the head, and to relieve any spasm or strain to which the neck muscles may be subjected by transmitting weight or force from the head to the shoulders or adjacent area.

Other collars are intended to be used where near complete immobilization of the head and neck are necessary. There exist presently a multitude of cervical collars intended to perform one or more of the above-mentioned functions.

U.S. Pat. No. 3,572,328 to John L. Bond describes an adjustable, flexible cervical collar designed for universal use by providing vertically adjustable movable sections displaceable relative to each other and to a base portion.

U.S. Pat. No. 2,911,970 to W. L. Bartles pertains to a cervical collar having two-piece construction which allows for adjustment of the forward portion of the cervical collar. This allows for the use of a single collar by persons having different length necks, as measured in the front of the person.

U.S. Pat. No. 3,916,885 pertains to a cervical collar where the entire height of the collar is adjustable to provide a single collar for persons having different length necks.

While prior art cervical collars have had various measures of success in immobilizing the head and neck of a patient, there are several problems associated with such collars. First, there has heretofore been a trade-off between immobilizing the head and neck of a patient and patient comfort while wearing the collar. In order to increase the degree of immobilization, collars were made more rigid between the patient's chin, shoulders, sternum, and upper back. This resulted in pressure points and discomfort to the patient.

Prior art collars have not provided optimum immobilization of the patient. Attempts to provide better immobilization have heretofore met with only limited success on an extended-wear basis. Frequently, attempting to further immobilize a patient's head and neck will result in added pressure where the collar rests upon the patient's chest or supports the jaw. Further, the pressure required to immobilize a patient is generally distributed over a very small area, creating pressure points. While these pressure points are uncomfortable for the patient, they present a more serious problem in that such pressure points tend to lead over time to contraction of decubitus by the patient. Therefore, prior art collars have not been suitable for long term immobilization of a patient.

Decubitus or decubitus ulcers (also known as bed sores, pressure sores, or trophic ulcers) arise when tissues overlying a bony prominence have been subjected to prolonged pressure against an external object, in this case a cervical collar. Decubitus is basically a breakdown of the tissue overlying the bone. Decubitus ulcers can affect not only superficial tissues such as skin, but also muscle and bone. Several factors contribute to the formation of decubitus. Moisture and pressure are two of the major contributing factors to the formation of decubitus ulcers. Once a decubitus ulcer forms, the ulcer is like an iceberg, a small visible surface with an extensive unknown base. There is no good method of determining the extent of tissue damage. Once decubitus has started, it will continue to progress through the skin and fat tissue to muscle, and eventually bone. Once started, decubitus is very difficult to treat and arrest. In extreme cases, surgical replacement of bone, muscle and skin are required to restore that portion of a patient which suffers from decubitus.

SUMMARY OF THE INVENTION

The present invention provides a cervical collar which reduces the likelihood of contracting decubitus in a patient wearing such collar, yet increases the degree of immobilization achieved by redistributing the pressure needed to immobilize the patient's head and cervical spine.

The present invention comprises a cervical collar having front and rear semi-rigid portions. The front portion comprises a semi-rigid preformed jaw support contoured to follow the jaw line of a patient, and a preformed sternum brace contoured to contact the sternum and upper trapezius of the patient and to support the jaw support. The rear portion of the cervical collar is contoured to follow the curve of the back of the head or occiput and to support the head and neck. The sternum brace has right, left, and central sections, wherein the height of the central section is adapted to correspond to the distance between a patient's sternum and jaw at the chin and the height of the right and left sections is adapted to correspond to the distance between a patient's upper trapezius and jaw. The height of the right and left sections is independent of the height of the central section. Further, the jaw support preferably includes a cushioning pad and a covering of antidecubitus material.

In a preferred embodiment, the jaw support of the collar is adjustable, to adjust to the natural angle of the patient's jaw, and the right and left sternum brace portions have recesses which prevent the collar from placing excessive pressure on the clavicle of the patient. Also, the particular design of the collar varies with the intended use, as between a patient who will be mobile and a patient who will be bedridden.

DETAILED DESCRIPTION OF THE FIGURES

Figure 1:
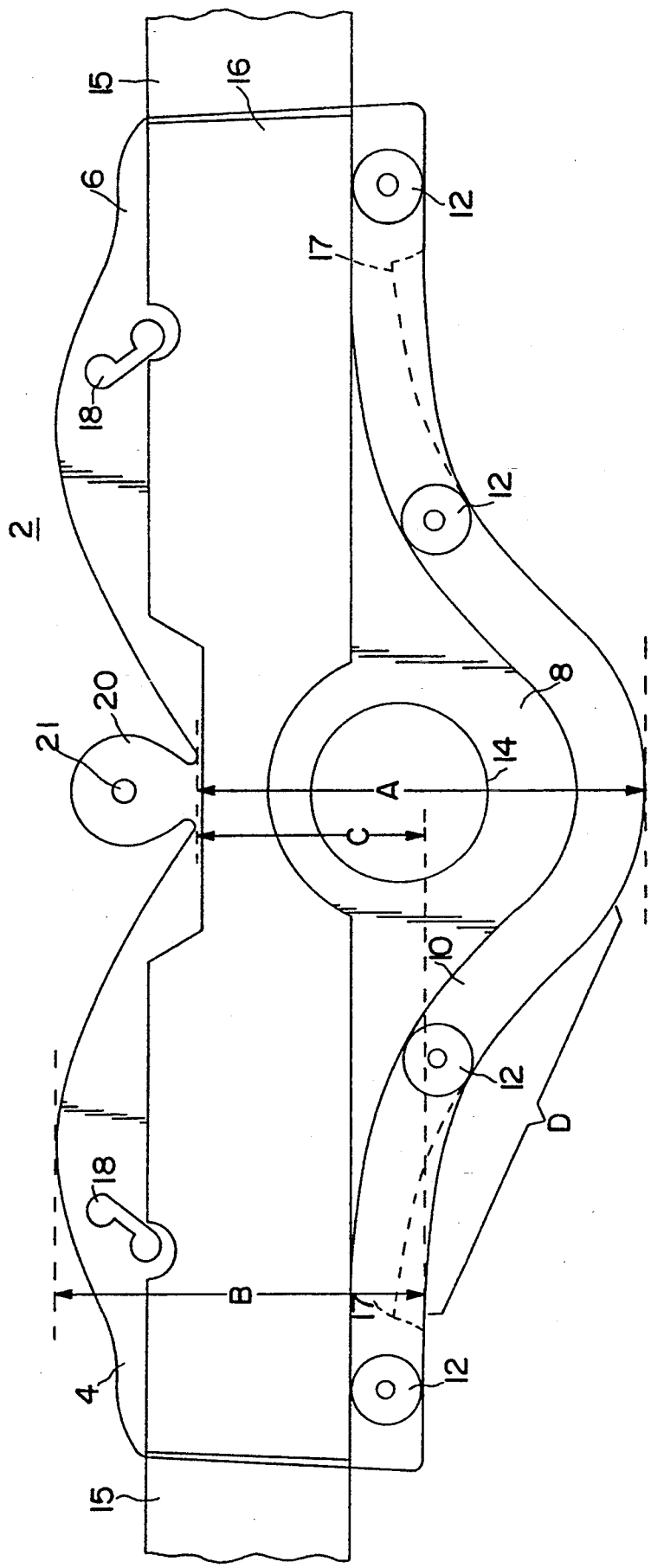
FIG. 1 is a plan view of the sternum brace of the front semi-rigid portion of a cervical collar of the present invention.

Referring now to FIG. 1, preformed sternum brace 2 comprises left, right and central portions 4, 6 and 8, respectively. Preformed sternum brace 2 is generally made from some semi-rigid materials such as low density polyethylene. Sternum brace 2 is generally symmetrical about a center line. Sternum brace 2 includes continuous padding 10 along the entire lower portion thereof, where the sternum brace will contact the sternum and upper trapezius of a patient. This padding may be made from a material such as expanded polyurethane or neoprene with a low durometer. Padding 10 is secured to sternum brace 2 by plastic rivets 12. Preferably, these rivets are snapped together for ease of assembly, but may also be hot welded or made of any other suitable construction. Padding 10 may also be secured to sternum brace 2 by adhesive or other conventional means. The remainder of sternum brace 2 is generally left unpadded as it does not usually contact the body of the patient. Preformed sternum brace 2 is also equipped with suitable hook and loop fastener material 16 for easy placement and securing on the patient. Retaining strap 15 serves to facilitate application of the collar to a patient by holding sternum brace 2 loosely in position around the patient's neck before back support 32 is applied.

Cervical collars, such as those of the present invention, are often used for trauma patients who have injuries in addition to injuries of the neck, or need more care than just a cervical collar. Some of those patients may for instance require a tracheotomy, which might prevent use of a cervical collar, which would cover the patient's throat. Therefore, preformed sternum brace 2 includes opening 14 which allows for access to the patient's throat or allows access to a tracheal tube when necessary. Very often, when trauma patients are in need of cervical collars such as the collar of the present invention, associated problems also arise.

Preformed sternum brace 2 is also equipped with multi-position openings 18 which provide for attachment and adjustment of a semi-rigid preformed jaw support 3 to preformed sternum brace 2. Also for this attachment is single position opening 21 in tab 20 of preformed sternum brace 2.

Figure 2:
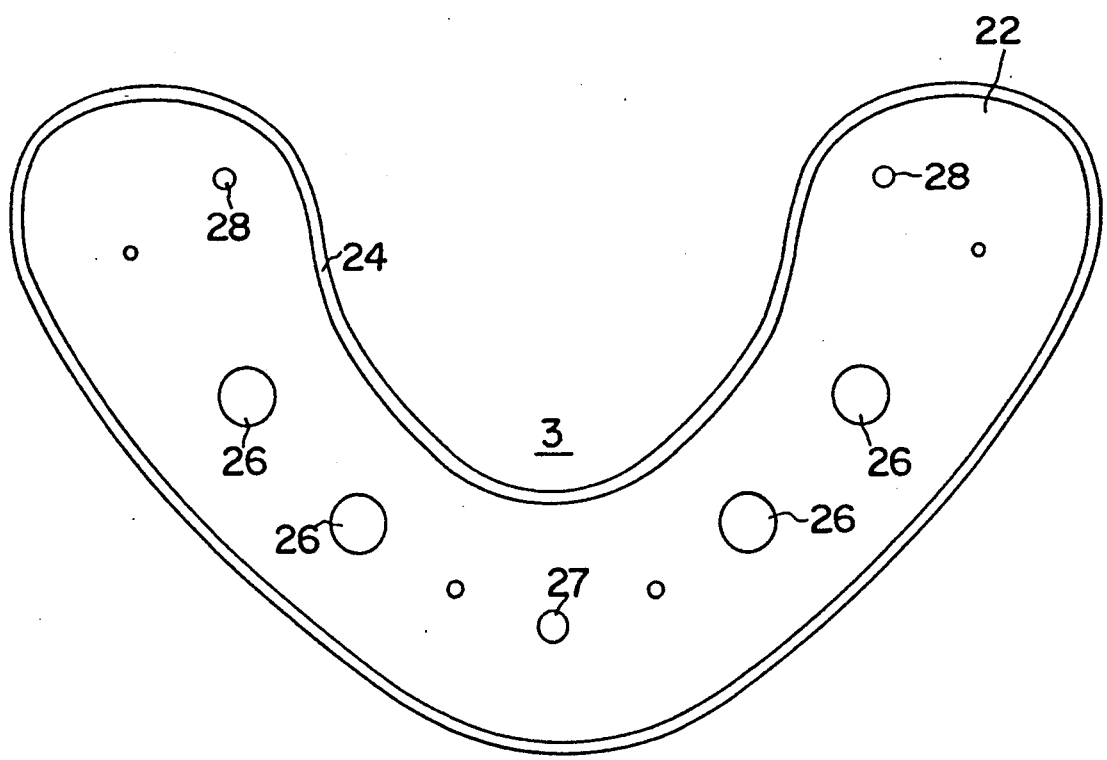
FIG. 2 is a plan view of the jaw support of the front semi-rigid portion of a collar of the present invention.
Figure 3:
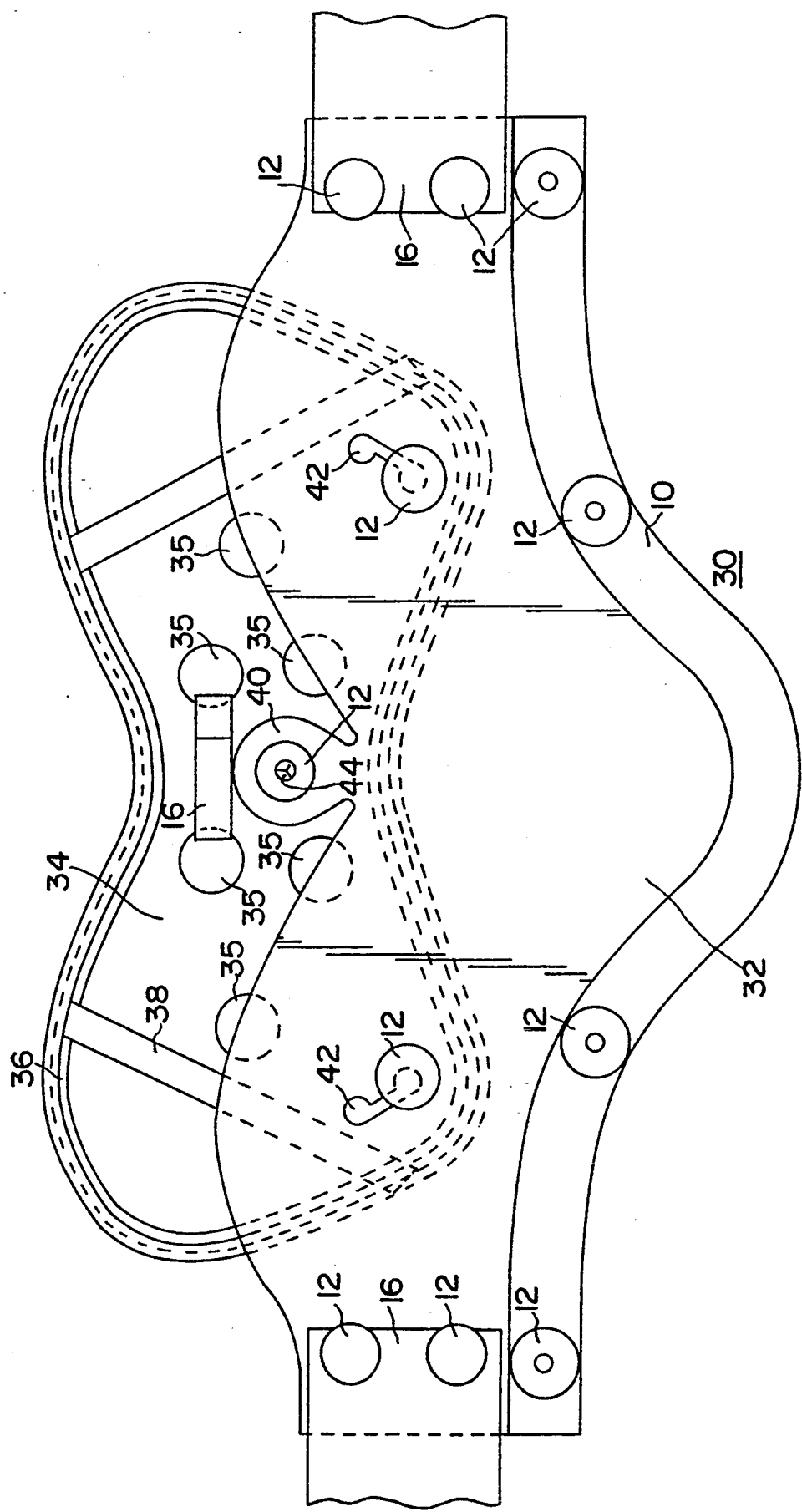
FIG. 3 is a plan view of the rear semi-rigid portion of the collar of the present invention.
Figure 4:
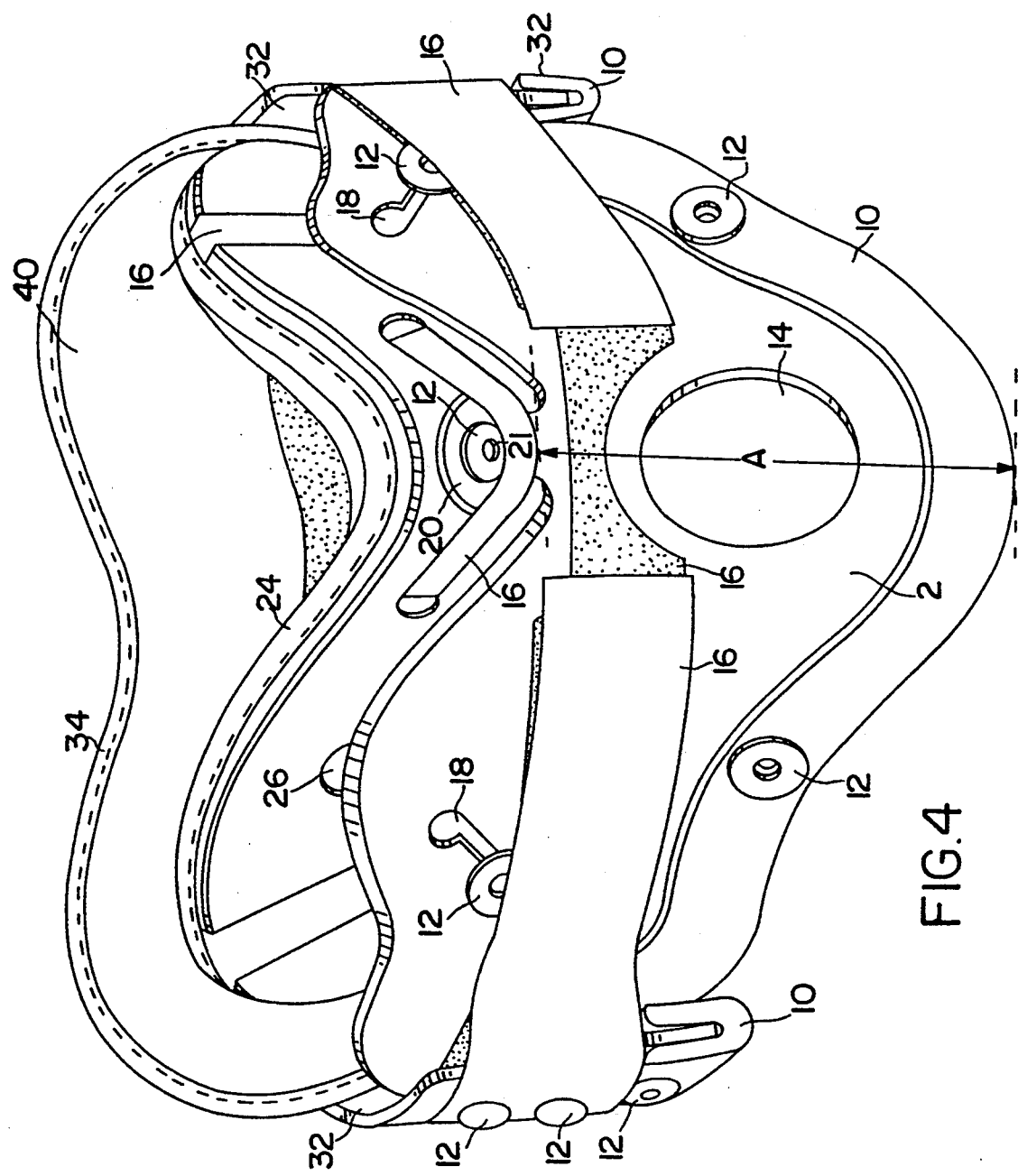
FIG. 4 is a perspective view of the collar of the present invention.

Semi-rigid preformed jaw support 3 is shown in FIG. 2. Preformed jaw support 3 comprises a backing 22 of a suitable semi-rigid material such as low density polyethylene and a porous foam pad 24 secured to backing 22. Backing 22 is equipped with several vent holes 26 to allow for the passage of moisture into and out of porous foam pad 24. Porous foam pad 24 should be made from an open cell material to provide for air circulation to the skin of the patient. Vent holes 26 also allow attachment of foam pad 24 by means of hook and loop fasteners 16 as shown in FIGS. 3 and 4. Any other suitable releasable means of attachment may be used to attach foam pad 24 to backing 22 such as buttons or snaps. Semi-rigid preformed jaw support 3 also includes openings 27 and 28 for attachment to preformed sternum brace 2. Opening 27 and opening 21 are attached together with a rivet (not shown) such as plastic rivets 12 which secure continuous padding 10 to preformed sternum brace 2. Openings 28 are secured through the use of plastic rivets to multiposition openings 18 in preformed sternum brace 2. This allows for adjustment of jaw support 3 with respect to preformed sternum brace 2 by positioning the angulation of jaw support 3 in relation to sternum brace 2 to match the natural angulation of the patient's jaw, an even distribution of pressure is promoted by more accurately forming the brace to the patient's anatomy.

Figure 10:
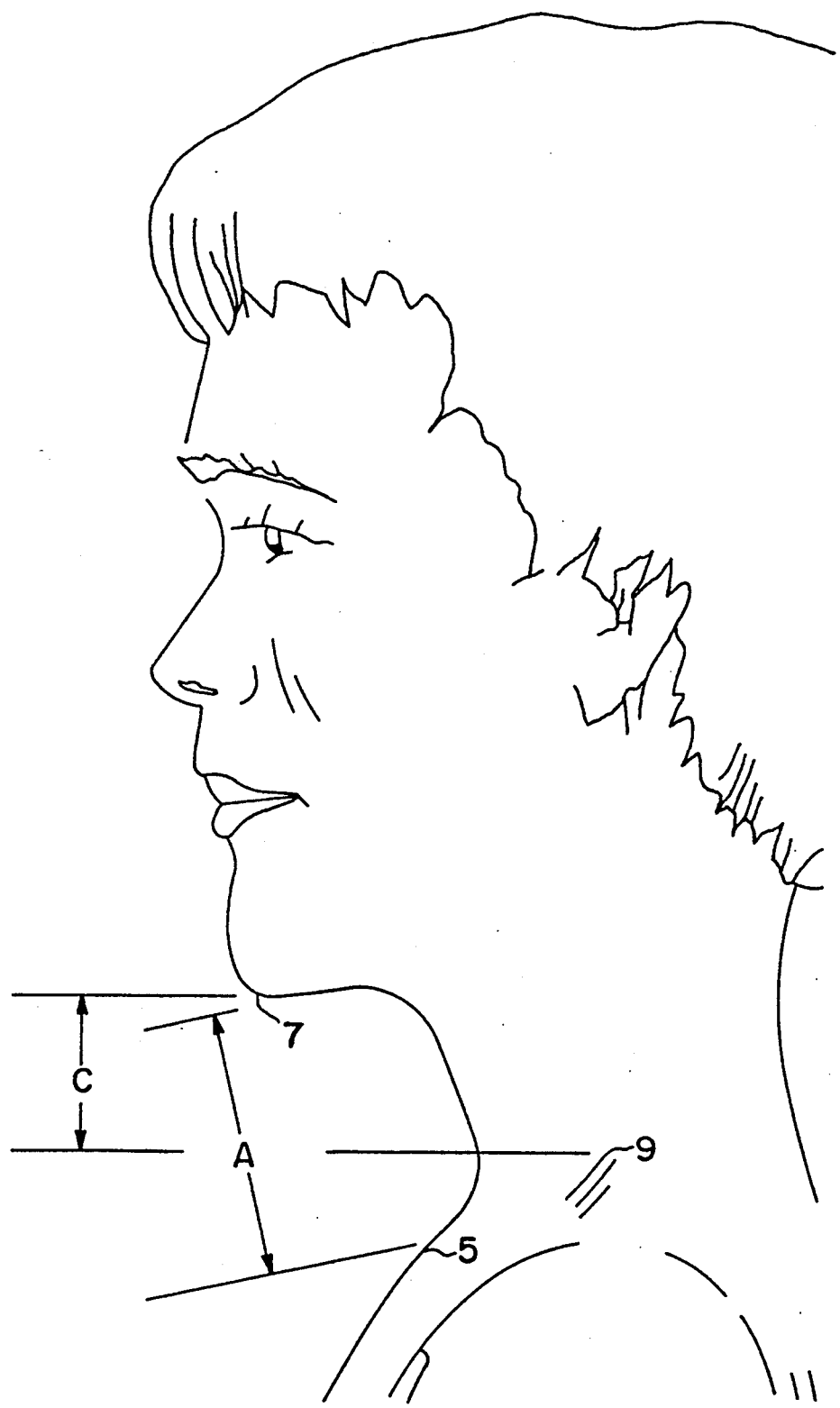
FIG. 10 is a side view of a patient to be fitted with a collar of the present invention.

Height A of center section 8 of preformed sternum brace 2 is selected to be the same as the distance from the patient's sternum 5 to the underside of the patient's jaw at the chin. Height B of left or right section 4 or 6 of sternum brace 2, and specifically distance C is selected to be the height from the patient's upper trapezius to the patient's jaw at the chin. Distance C is equal to the difference in height of the patient's upper trapezius 9 and the patient's jaw at the chin 7, as shown as distance C in FIG. 10. These height A and distance C (and height B) are independently calculated from one another. Thus, two patients, with long necks (as calculated from the jaw near the chin to the sternum) may require cervical collars with identical heights A, but different distances C if the patient's shoulders are of different sizes. A patient with larger shoulders will have a shorter distance C between the upper trapezius and jaw than a patient with smaller shoulders.

The improvement occasioned by the independent calculation of distances A and C arises from three specific areas: first, it allows more even support of the brace on the sternum and upper trapezius of the patient and smaller chance of movement of the support; second, it allows more even spreading of the pressure to the jaw of the patient to maintain the patient's head in a neutral alignment with respect to the remainder of the patient's body; third, this allows the collar to rest on the sternum and upper trapezius while placing little or no pressure on the clavicle due to recess 17 which is specifically cut out to form an arch over the clavicle. Pressure on the clavicle by prior art collars is a major contributor to decubitus in the patient. By contrast, the collar of the present invention has been cut around the clavicle in the area D, specifically to eliminate pressure on the clavicle. This creates fewer pressure points all around the patient, and allows greater total pressure to be transferred to the patient's head to limit movement thereof. Thus, the patient's head is more rigidly held, yet more comfortably.

The elimination of pressure points is critical to the elimination of decubitus in the patient. More even distribution of the pressure transferred from the patient's body to the patient's head, or vice versa, thus substantially reduces the likelihood of contraction of decubitus, and the severity thereof if contracted.

While this aids in reduction and elimination of decubitus, it was found that still further reduction could be accomplished by the use of appropriate materials in the production of a collar. Porous foam pad 24 has an outer covering 25 which directly contacts the skin of the patient. The material used for covering 25 may help prevent decubitus. Specifically, where foam pad 24 is permanently attached to backing 22, foam pad 24 can have an outer covering of a material which allows passage of vapor but not of liquid. The material is microporous and stretchable. The preferred material for use as a covering 25 for foam pad 24 is DARLEXX ™ from Darlington Fabrics, Providence, R.I. Where foam pad 24 may be removed and changed as necessary, cover 25 need not be made from vapor permeable/liquid impermeable material. The preferred material in this case is DURASORB ™ from Quimet Corporation of Nashville, Tenn. DURASORB ™ is not a liquid impermeable/vapor permeable material instead it functions to wick moisture away from its source thereby promoting rapid evaporation of moisture and significantly reducing drying time of the padding. Its use should be limited to those instances where the foam padding 24 and 25 may be periodically replaced, as when the collar is used for extended periods of time where the patient is ambulatory. Periodic removal and replacement of the padding for drying or hygienic purposes will greatly reduce the incidence of decubitus.

However, where the collar should not be removed or the padding is not replaceable, as in the alternative embodiment to be explained presently, the padding should be covered with DARLEXX ™ which is a liquid impermeable/vapor permeable material. This allows vapor to pass in and out and allows the skin to breathe and dispose of moisture through evaporation while preventing the padding from becoming soaked with liquid. Wet padding against the skin of a patient is very conducive to decubitus and should be avoided whenever possible. Thus, the use of a liquid impermeable/vapor permeable material is very useful in reducing the chance of developing decubitus. This is important where the collar cannot be removed or when a patient is bedridden, such as in the intensive care ward of a hospital.

Referring now to FIG. 3, semi-rigid portion 30 comprises back support 32 and head support 34. Both back support 32 and head support 34 are made from a semi-rigid material such as low density polyethylene. Back support 32 includes continuous padding 10 along the bottom portion thereof where the back support 32 is intended to contact the body of the patient. Back support 32 also includes recesses 33 to avoid placing pressure on the soft tissue of the back portion of the trapezius muscle and to distribute pressure to the upper back along the spine which serves to provide greater immobilization and patient comfort. Continuous padding 10 is held in place by plastic rivets 12. Adhesive attachment may also be used. Also attached to back support 32 by plastic rivets 12 is hook and loop fastener material 16 which is used to secure back support 32 to preformed sternum brace 2.

Head support 34 includes several vents 35 which allow for passage of vapor from pad 36 through the semi-rigid material. Vents 35 also allow for attachment of pad 36 by cloth straps 38 and by hook and loop fastener material 16. Head support 34 is attached to back support 32 by rivets 12 through multi-position openings 42 and single position opening 44. Multi-position openings 42 allow for adjustment of head support 34 for different size heads of patients, and to allow adjustment of the angulation of head support 34 to assure proper and even pressure across the occiput of the patient.

Figure 5:
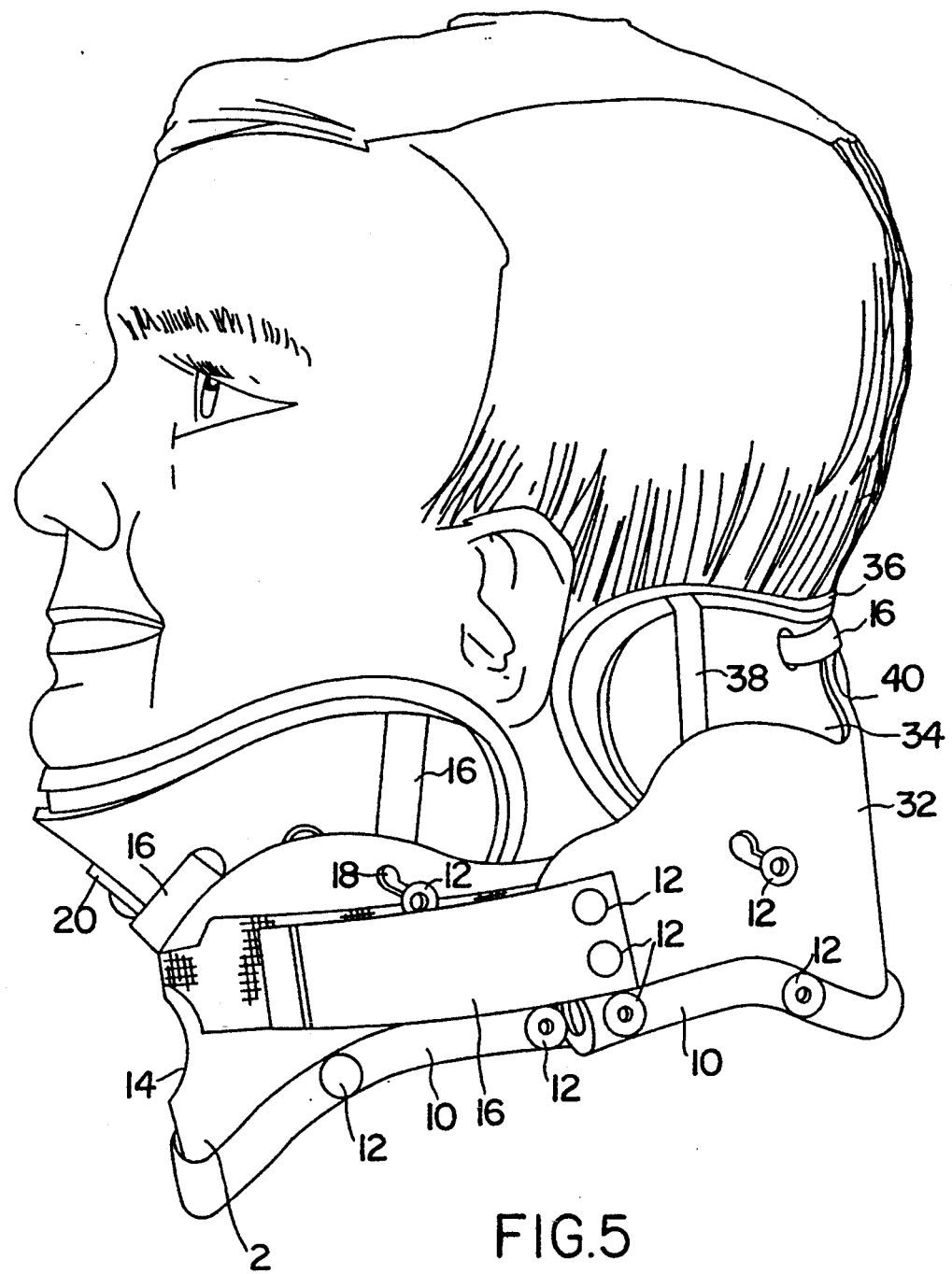
FIG. 5 is a side view of the collar of the present invention fitted to a patient.

The entire assembled cervical collar of the present invention is shown in FIGS. 4 and 5. Thus the entire configuration as assembled and the interaction of different portions with each other and the patient may be seen as a whole in FIGS. 4 and 5.

When a patient is fitted with a cervical collar such as a collar of the present invention, the collar should be adjusted so that the patient's head is held in a desired alignment front to back. The collar configuration shown in FIGS. 1 through 5 performs such a function when the patient is in an upright position. However, if the patient is to be bedridden and in a supine position, the configuration of the human anatomy is different than it is when upright, therefore, the configuration (but not the basic design) of the collar should be altered to provide for a reduced distance from the chin to the sternum. Further, a less rigid rear support may be used since freedom of movement rearwardly will naturally be severely restricted by the bed or other surface upon which the patient is resting; a rigid back piece will produce unwanted pressure points. Such a configuration is embodied in the collar shown in FIGS. 6 through 9.

Figure 6:
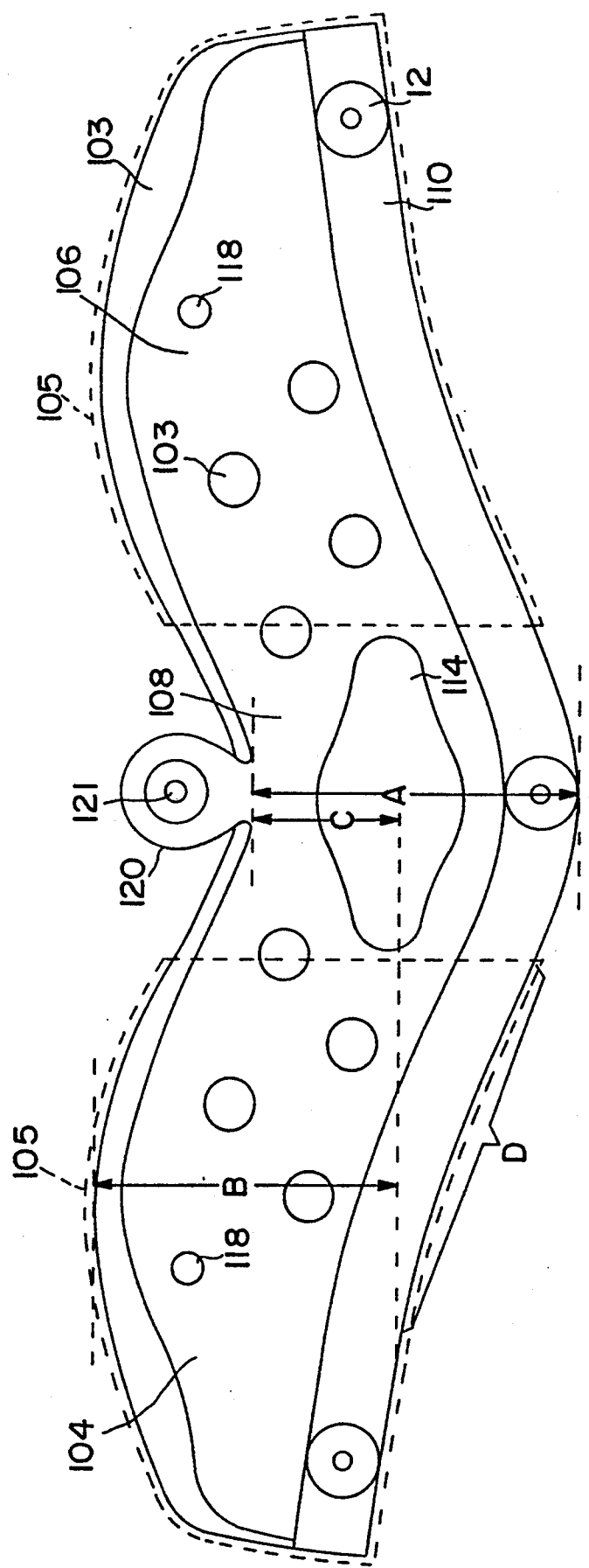
FIG. 6 is a plan view of the alternate embodiment of the sternum brace of the front portion of the collar of the present invention.
Figure 7:
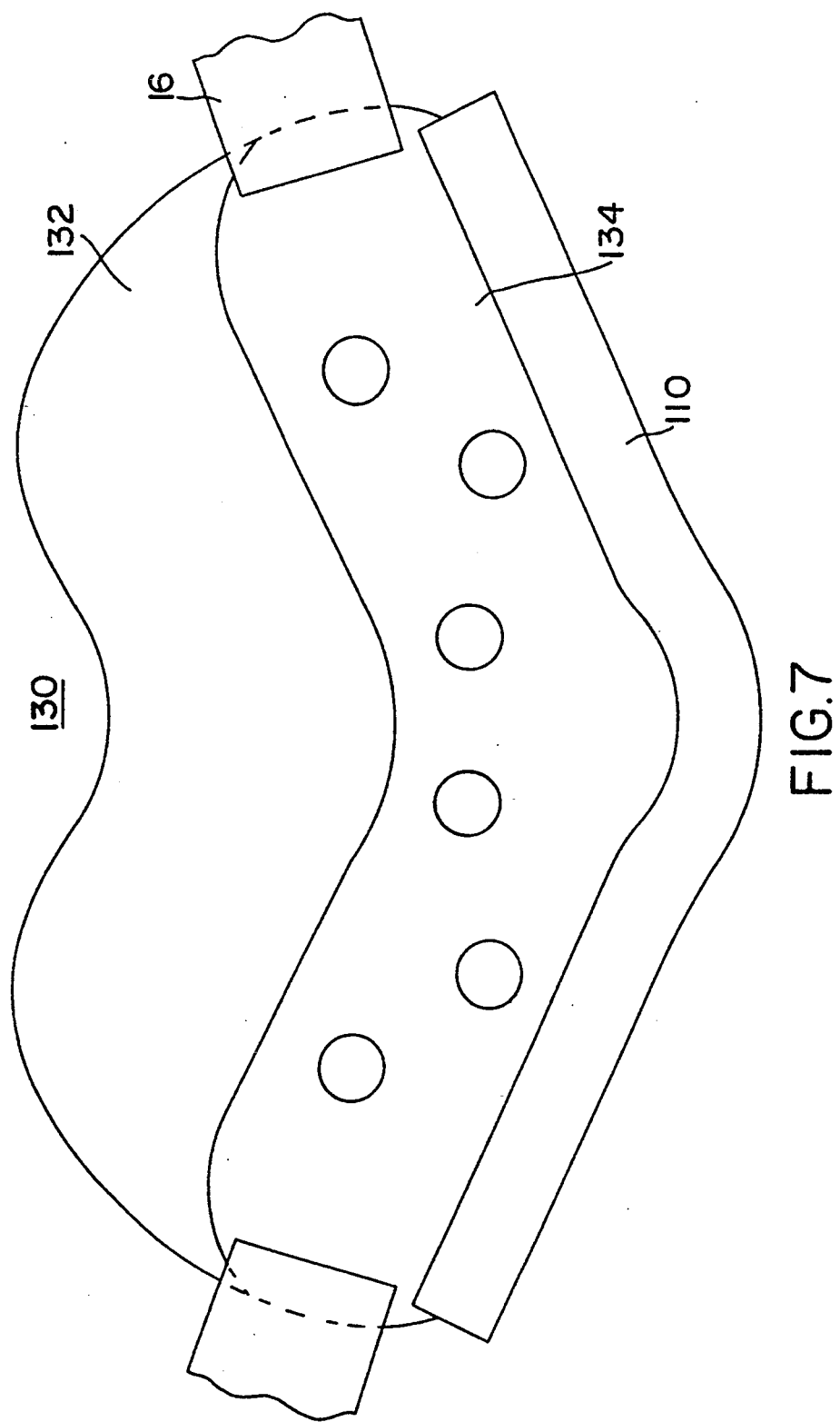
FIG. 7 is a plan view of the alternate embodiment of the rear semi-rigid portion of the collar of the present invention.
Figure 8:
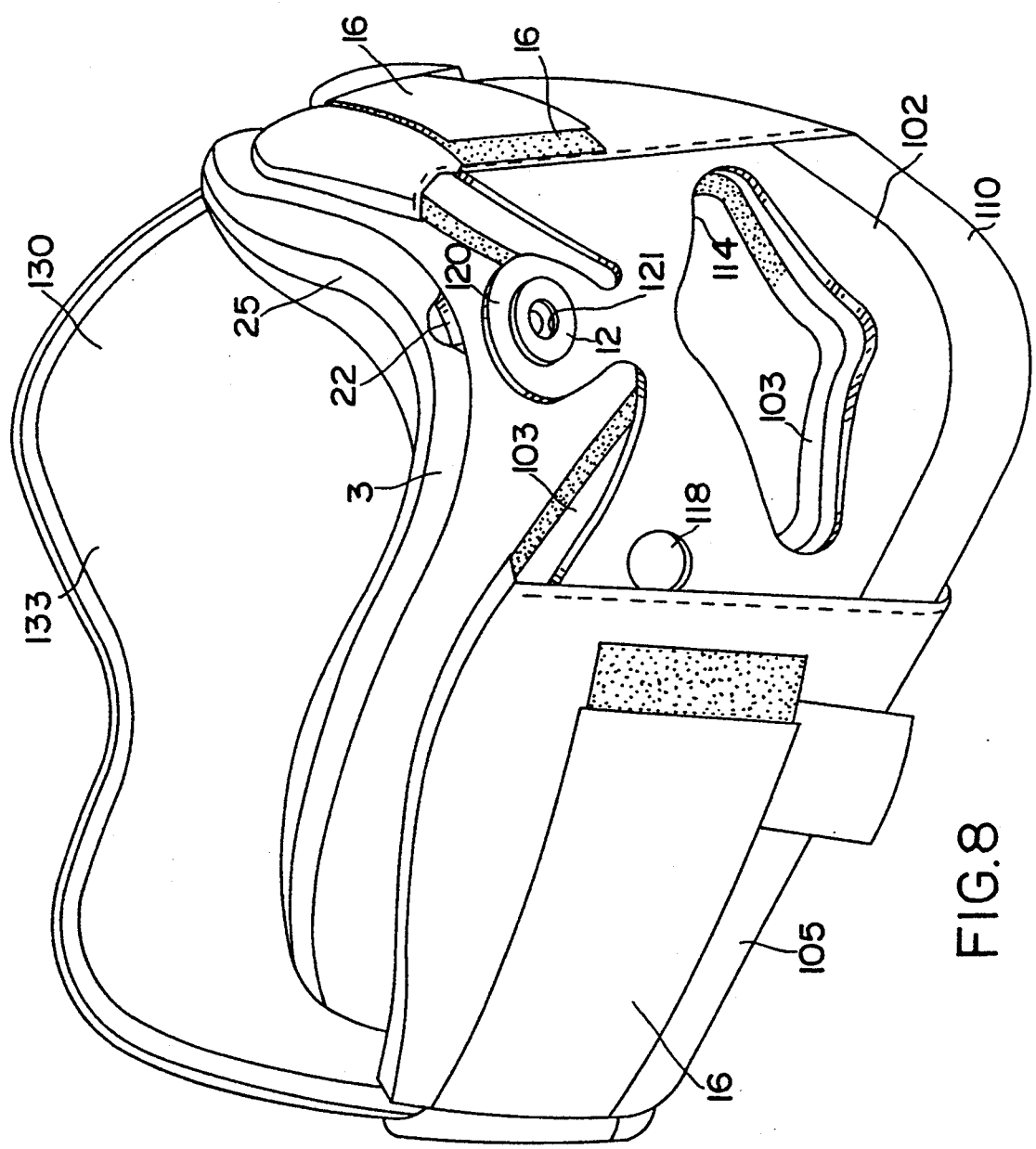
FIG. 8 is a perspective view of the alternate embodiment of the collar of the present invention.
Figure 9:
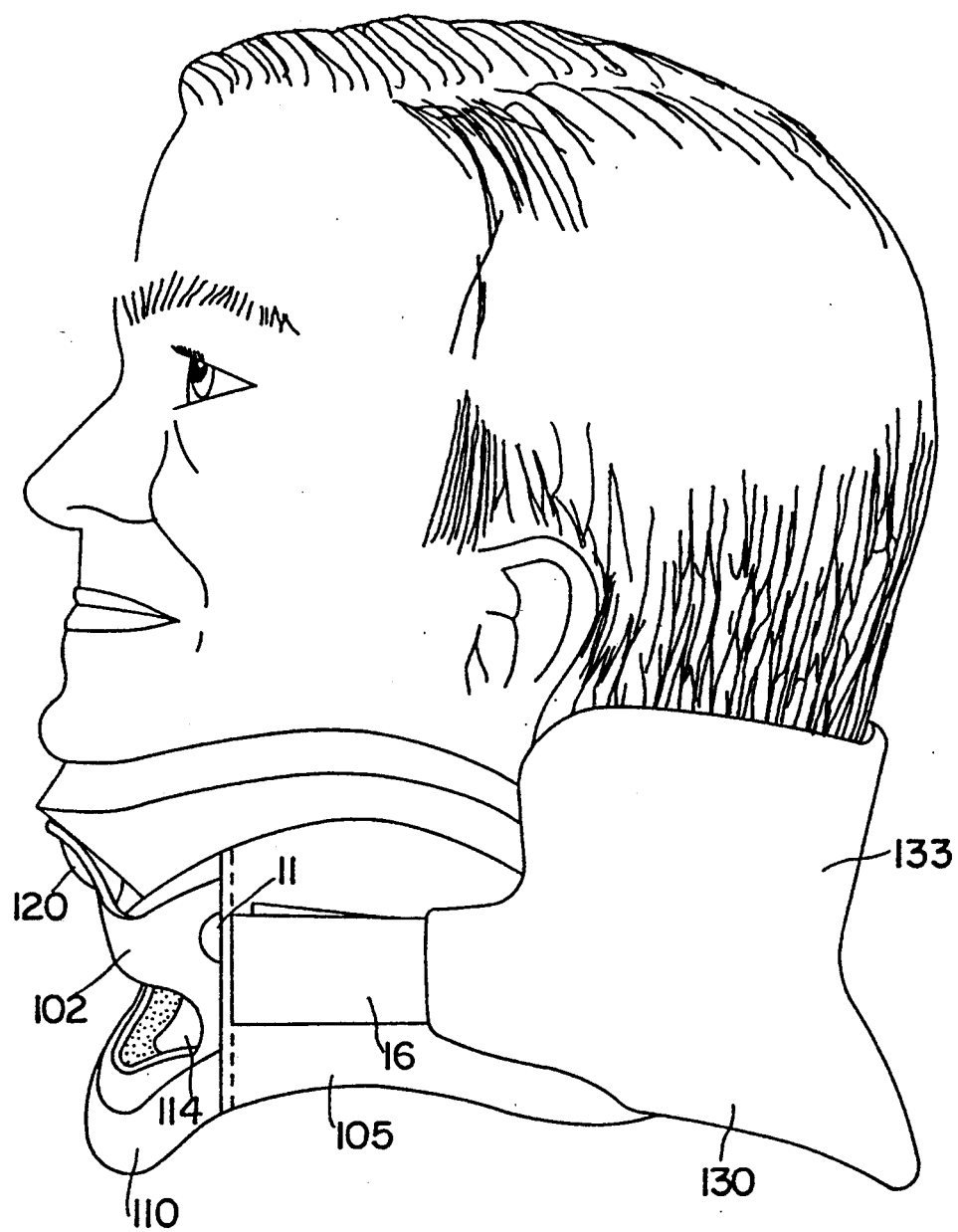
FIG. 9 is a side view of the alternate embodiment of the collar of the present invention fitted to a patient.

FIG. 6 shows a preformed sternum brace 102 of an alternative configuration of the collar of the present invention. Preformed sternum brace 102 comprises left, right and central portions 104, 106 and 108, respectively. Sternum brace 102 is preferably made from some semi-rigid material such as low density polyethylene and is generally symmetrical about a center line. Sternum brace 102 is similar to preformed sternum brace 2, but the distances A, B and C have been specifically calculated for a supine patient. This includes a reduction of distances A and C as a supine patient will have a smaller distance from chin to sternum. Sternum brace 102 includes continuous padding 110 along the entire lower portion thereof, secured to sternum brace 102 by plastic rivets 112 or adhesive or other conventional means, and opening 114 which allows for access to the patient's throat or a tracheal tube if present.

Sternum brace 102 also differs from sternum brace 2 in that sternum brace 102 lacks multi-position openings 18. Instead sternum brace 102 includes single position openings 118, which, along with single position opening 121 on tab 120, allow for attachment of preformed jaw support 3. This is the same preformed jaw support shown in FIG. 3 which is used for the collar shown in FIGS. 1 through 5. In this case, however, foam pad 24 is not removable. Foam pad 24 is permanently attached to backing 22 by adhesive or other suitable attachment means. Further, outer covering 25 is also permanently attached to foam pad 24 and backing 22, and is preferably made from DARLEXX ™. This provides a vapor permeable, liquid impermeable barrier which allows foam pad 24 to "breathe" and prevents it from becoming soaked with liquid. This greatly reduces the chance of the patient contracting decubitus Sternum brace 102 also includes padding 103 across the entire rear surface thereof. Accordingly, sternum brace 102 includes sternum brace cover 105. The sternum brace cover is shown in FIG. 6 in outline so that the sternum brace 102 may be more clearly and easily seen. Sternum brace cover 105 is held in place be adhesive or other appropriate means of attachment. Once preformed jaw support 3 is attached to sternum brace 102, the sternum brace cover 105 is locked in place. Sternum brace cover 105 is made from DARLEXX ™ to prevent the pad from becoming soaked. Sternum brace cover 105 includes hook and loop fastener material 16 to allow for attachment of the collar to the patient and for attachment to rear semi-rigid portion 130.

Rear semi-rigid portion 130 comprises head support 134 and padding 132. Rear semi-rigid portion 130 includes continuous padding 110 along the entire lower portion thereof, secured to portion 130 by plastic rivets 112 (not shown) or adhesive or other conventional means. Hook and loop fastener material 16 is included to allow attachment to sternum brace 102. The entirety of rear semi-rigid portion 130 is also covered with a DARLEXX ™ cover 133 to prevent padding 132 from becoming soaked. That covering has not been shown for ease of viewing of semi-rigid portion 130. Rear semi-rigid portion 130 has only limited support and stiffness, since it is designed for a supine patient, and the surface upon which the patient rests will provide any further support necessary. If, for some reason, more support is needed than would otherwise be achieved by rear semi-rigid portion 130, a removable rigid occipital support made from suitable material such as low density polyethylene in the shape of foam pad 132, may be added inside of antidecubitus DARLEXX ™ cover 133 to provide added occipital and lateral support.

It is understood that various other modifications will be apparent to one skilled in the art without departing from the spirit and scope of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A cervical collar comprising:

front and back semi-rigid portions, each having a fixed height;

said front portion comprising a semi-rigid preformed jaw support contoured to follow the jaw line of a patient, and a preformed sternum brace contoured to contact the sternum and upper trapezius of the patient and support said jaw support;

said back portion contoured to follow the curve of and to support the back of the neck and occiput;

said sternum brace having right and left sections, adapted to rest upon the upper trapezius of the patient and to contact and support the patient's jaw when the head of said patient is in a preferred, predetermined alignment;

said sternum brace also having a central section adapted to rest upon the patient's sternum and to contact and support said jaw support while said jaw support contacts and supports the patient's jaw, when the head of said patient is in a preferred, predetermined alignment; and said jaw support including a removable foam pad.

2. The cervical collar of claim 1 wherein said jaw support includes a pad having a cover of antidecubitus material.

3. The cervical collar of claim 2 wherein said antidecubitus material is a stretchable, microporous material.

4. The collar of claim 1 wherein said right and left sternum brace sections each include a recess adapted to form an arch around the clavicle of a wearer.

5. The cervical collar of claim 1 wherein said back portion comprises a back support and a head support, said back support having multi-position openings for attachment and adjustment of said head support.

6. The collar of claim 5 wherein said back support includes a removeable foam pad.

7. The collar of claim 1 wherein said back portion further includes a removable semi-rigid rear head support.

* * * * *